(12) United States Patent
Holinstat et al.

(10) Patent No.: US 11,236,044 B2
(45) Date of Patent: Feb. 1, 2022

(54) SELECTIVE INHIBITORS OF 12(S)-LIPOXYGENASE (12-LOX) AND METHODS FOR USE OF THE SAME

(71) Applicant: THE REGENTS OF THE UNIVERSITY OF MICHIGAN, Ann Arbor, MI (US)

(72) Inventors: Michael Holinstat, Ann Arbor, MI (US); Reheman Adili, Ypsilanti, MI (US); Andrew White, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/047,427

(22) PCT Filed: Apr. 17, 2019

(86) PCT No.: PCT/US2019/027785
§ 371 (c)(1),
(2) Date: Oct. 14, 2020

(87) PCT Pub. No.: WO2019/204375
PCT Pub. Date: Oct. 24, 2019

(65) Prior Publication Data
US 2021/0147348 A1 May 20, 2021

Related U.S. Application Data

(60) Provisional application No. 62/658,936, filed on Apr. 17, 2018.

(51) Int. Cl.
*C07C 311/44* (2006.01)
*C07D 209/40* (2006.01)
*A61P 7/02* (2006.01)

(52) U.S. Cl.
CPC .............. *C07C 311/44* (2013.01); *A61P 7/02* (2018.01); *C07D 209/40* (2013.01); *C07C 2601/02* (2017.05)

(58) Field of Classification Search
CPC ........................... C07C 311/44; C07D 209/40
See application file for complete search history.

(56) References Cited

U.S. PATENT DOCUMENTS

2007/0105825 A1    5/2007   Hoyano et al.

FOREIGN PATENT DOCUMENTS

WO         2015/054662 A1    4/2015

OTHER PUBLICATIONS

Adili et al., First Selective 12-LOX Inhibitor, ML355, Impairs Thrombus Formation and Vessel Occlusion In Vivo With Minimal Effects on Hemostasis, Arterioscler Thromb. Vasc. Biol., 37(10):1828-1839 (2017).
Berge et al., Pharmaceutical Salts, J. Pharm. Sci., 66(1):1-19 (1977).
Filippova et al., Synthesis of obscuraminol A using an organocatalyzed enantioselective Henry reaction, Tetrahedron, 72(41):6572-6577 (2016).
Ghosh et al., Inhibition of arachidonate 5-lipoxygenase triggers massive apoptosis in human prostate cancer cells, Proc. Natl. Acad. Sci U.S.A, 95(22):13182-13187 (1998).
Go et al., Executive summary: heart disease and stroke statistics—2014 update: a report from the American Heart Association, Circulation, 129(3):399-410 (2014).
International Application No. PCT/US19/27785, International Preliminary Reporton Patentability, dated Oct. 29, 2020.
International Application No. PCT/US19/27785, International Search Report and Written Opinion, dated Jun. 13, 2019.
Kenyon et al., Discovery of potent and selective inhibitors of human platelet-type 12-lipoxygenase, J. Med. Chem., 54(15):5485-5497 (2011).
Lkei et al., Investigations of human platelet-type 12-lipoxygenase: role of lipoxygenase products in platelet activation, J. Lipid Res., 53(12):2546-2559 (2012).
Luci et al., Synthesis and structure-activity relationship studies of 4-((2-hydroxy-3-methoxybenzyl)amino)benzenesulfonamide derivatives as potent and selective inhibitors of 12-lipoxygenase, J. Med. Chem., 57(2):495-506 (2014).
Ruggeri, Platelets in atherothrombosis, Nat. Med., 8(11):1227-1234 (2002).
Steele et al., Lipoxygenase inhibitors as potential cancer chemopreventives, Cancer Epidemiol Biomarkers Prev., 8(5):467-483(1999).
Steg et al., Atherothrombosis and the role of antiplatelet therapy, J. Thromb. Haemost., 9(suppl 1):325-332 (2011).
Yeung et al., 12-lipoxygenase activity plays an important role in PAR4 and GPVI-mediated platelet reactivity, Thromb. Haemost., 110(3):569-581 (2013).
Zheng et al., Analgesic agents without gastric damage: design and synthesis of structurally simple benzenesulfonanilide-type cyclooxygenase-1-selective inhibitors, Bioorg. Med. Chem., 15(2)1014-1021 (2007).

*Primary Examiner* — Shawquia Jackson
(74) *Attorney, Agent, or Firm* — Marshall, Gerstein & Borun LLP

(57) ABSTRACT

Disclosed herein are small molecule inhibitors of 12(S)-Lipoxygenase (12-LOX), and methods of using the small molecules to inhibit 12-LOX activation and to treat diseases, such as platelet hemostasis and thrombosis. In particular, disclosed herein are compounds of Formula (I) and pharmaceutically acceptable salts thereof: wherein the substituents are as described.

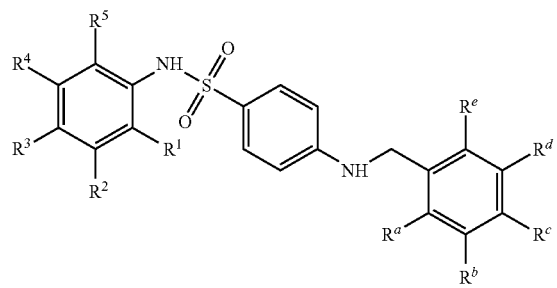

(I)

20 Claims, 3 Drawing Sheets

SELECTIVE INHIBITORS OF 12(S)-LIPOXYGENASE (12-LOX) AND METHODS FOR USE OF THE SAME

CROSS REFERENCE TO RELATED APPLICATION

This application claims priority to U.S. Provisional Patent Application No. 62/658,936, filed Apr. 17, 2018, the disclosure of which is hereby incorporated by reference in its entirety.

BACKGROUND

Technical Field

The present disclosure relates to small molecule inhibitors of 12(S)-Lipoxygenase ("12-LOX"), and methods of using the small molecules to inhibit 12-LOX activation and to treat diseases, such as platelet hemostasis and thrombosis.

Description of Related Technology

Platelet adhesion and aggregation at the site of vascular injury are essential for maintaining normal hemostasis and preventing blood loss. However, the same processes can also lead to the development of arterial thrombosis and vessel occlusion when the integrity of the vessel wall is compromised by rupture of an atherosclerotic plaque. See Ruggeri Z M, Nat Med., 8:1227-1234 (2002). Excessive platelet activation and aggregation may lead to the formation of occlusive thrombi and result in severe consequences, such as myocardial infarction, ischemic stroke, and pulmonary embolism, which are the predominant causes of morbidity and mortality worldwide. See Go et al., Circulation, 129: 399-410 (2014). Antiplatelet therapy is considered a gold standard for its effectiveness in preventing aberrant platelet activation and pivotal in the treatment of cardiovascular atherothrombotic events to reduce morbidity and mortality. See Steg et al., J Thromb Haemost, 9(suppl 1):325-332 (2011). Currently approved antiplatelet therapies inhibit platelet function by targeting platelet enzymes, receptors, and glycoproteins. See Ikei et al., J. Lipid Res. 53:2546-2559 (2012). Although these therapeutic approaches limit platelet function, they often result in a concomitant increased risk of bleeding. Therefore, a need exists for the identification of novel antiplatelet therapeutic targets that limit bleeding.

Platelet 12(S)-lipoxygenase ("12-LOX"), an oxygenase predominantly expressed in human platelets, uses arachidonic acid released from the phospholipids as a substrate to form bioactive metabolites (12-(S)-hydroperoxyeicosatetraenoic acid and 12-(S)-hydroxyeicosatetraenoic acid (12(S)-HETrE)) that have been shown to regulate biological processes, such as integrin activation, vascular hypertension, and progression of certain types of cancer. See Steele et al., Cancer Epidemiol Biomarkers Prev, 8:467-483 (1999) and Ghosh et al., Proc Natl Acad Sci USA. 95:13182-13187 (1998). The bioactive lipid products resulting from 12-LOX oxidation have been shown to play a role in platelet activation, granule secretion, and clot retraction in vitro, suggesting an important role of 12-LOX in regulation of platelet function. See Ikei et al. Recently, a key role for 12-LOX activity has been identified in regulation of protease-activated receptor-4-mediated ("PAR4-mediated") and glycoprotein VI-mediated ("GPVI-mediated") signaling pathways in the platelet. See Kenyon et al., J Med Chem. 54:5485-5497 (2011); Luci et al., J Med Chem. 57:495-506 (2014); Yeung et al., Thromb Haemost. 110:569-581 (2013).

A 12-LOX inhibitor, ML355, shown below, was recently identified and has been shown to prevent thrombosis in vitro, with a >50-fold selectivity versus the paralogs, 5-human lipoxygenase, reticulocyte 15-human lipoxygenase type-1, and epithelial 15-human lipoxygenase type-2, and >100-fold selectivity versus bovine cyclooxygenase ("COX")-1 and human COX-2.

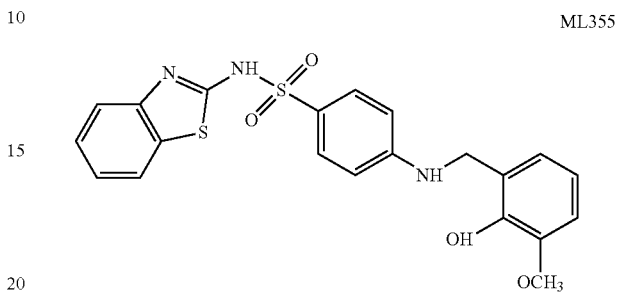

ML355

Further, 12-LOX was recently reported to be essential for FcγRIIa-mediated platelet activation, suggesting 12-LOX may also be a potential therapeutic target to limit immune-mediated thrombosis. See Luci et al. ML355 also has been shown to impair thrombus formulation and vessel occlusion in vivo with minimal affects on hemostasis. See Adili et al., Arterioscler Thromb Vasc Biol. 37(10):1828-1839 (2017). Therefore, ML355 treatment can be an ideal therapy targeting the pathogenesis of heparin-induced thrombocytopenia and thrombosis ("HITT") to prevent the onset, as well as limit the progression, of thrombotic complications of HITT because (1) inhibition of 12-LOX down regulates platelet reactivity and release of PF4 from platelet granules (2) inhibition of 12-LOX prevents FcγRIIa-dependent immune-mediated platelet activation and platelet clearance, and (3) ML355 inhibition of 12-LOX potently inhibits thrombosis without bleeding complications, which translates to a safer alternative to the currently clinical treatment with thrombin inhibitors. ML355 also has been shown to have reasonable pharmacokinetics, relatively good tolerance in preclinical studies, and can be given orally. However, ML355 suffers from limited solubility, which drastically diminishes its clinical use.

Therefore, there is a need for ML355 analogs capable of treating and/or preventing platelet hemostasis and thrombosis, which exhibit improved in vivo potency and solubility over ML355, without causing bleeding.

SUMMARY

Provided herein are compounds of Formula (I), or pharmaceutically acceptable salts thereof:

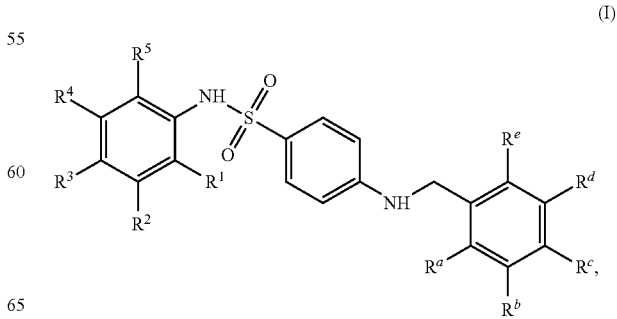

(I)

wherein: $R^2$ is halo, $C_{1-3}$fluoroalkyl, $C_{3-8}$fluorocyloalkyl, $OC_{1-3}$fluoroalkyl, or $OC_{3-8}$fluorocyloalkyl; each of $R^1$, $R^3$, $R^4$, and $R^5$ independently is H, halo, $C_{1-3}$fluoroalkyl, $C_{3-8}$fluorocyloalkyl, $OC_{1-3}$fluoroalkyl, or $OC_{3-8}$fluorocyloalkyl; each of $R^a$ and $R^b$ independently is OH, $OC_{1-3}$alkyl, $C_{1-3}$fluoroalkyl, $C_{3-8}$fluorocyloalkyl, $OC_{1-3}$fluoroalkyl, $OC_{3-8}$fluorocyloalkyl, or halo; each of $R^c$, $R^d$, and $R^e$ independently is H, OH, $OC_{1-3}$alkyl, $C_{1-3}$fluoroalkyl, $C_{3-8}$fluorocyloalkyl, $OC_{1-3}$fluoroalkyl, $OC_{3-8}$fluorocyloalkyl, or halo.

In some embodiments, $R^2$ is halo (e.g., Br, Cl, or F). In various embodiments, $R^2$ is Cl or F. In some cases, $R^2$ is Cl. In various cases, $R^2$ is $C_{1-3}$fluoroalkyl (e.g., $CH_2F$, $CHF_2$, or $CF_3$), $C_{3-8}$fluorocyloalkyl (e.g., cyclopropyl, cyclobutyl, cyclopentyl, or cyclohexyl substituted with F, $CH_2F$, $CHF_2$, or $CF_3$), $OC_{1-3}$fluoroalkyl, or $OC_{3-8}$fluorocyloalkyl. In some embodiments, $R^2$ is $CF_3$ or

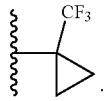

In some cases, each of $R^1$, $R^3$, $R^4$, and $R^5$ is H. In various cases, one or more of $R^1$, $R^3$, $R^4$, and $R^5$ is halo (e.g., Br, Cl, or F), $C_{1-3}$fluoroalkyl (e.g., $CH_2F$, $CHF_2$, or $CF_3$), $C_{3-8}$fluorocyloalkyl (e.g., cyclopropyl, cyclobutyl, cyclopentyl, or cyclohexyl substituted with F, $CH_2F$, $CHF_2$, or $CF_3$), $OC_{1-3}$fluoroalkyl, or $OC_{3-8}$fluorocyloalkyl.

In some embodiments, one or more of $R^1$, $R^3$, $R^4$, and $R^5$ is F, Cl, $CF_3$ or

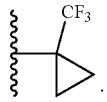

In various embodiments, $R^1$ is H or F; $R^2$ is Cl, $CF_3$, or

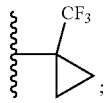

$R^3$ is H or F; $R^4$ is H; and $R^5$ is H.

In some cases, each of $R^a$ and $R^b$ independently is OH or $OC_{1-3}$alkyl. In various cases, one of $R^a$ and $R^b$ is OH or $OC_{1-3}$alkyl; and the other of $R^a$ and $R^b$ is $C_{1-3}$fluoroalkyl, $C_{3-8}$fluorocyloalkyl, $OC_{1-3}$fluoroalkyl, $OC_{3-8}$fluorocyloalkyl, or halo. In some embodiments, $OC_{1-3}$alkyl is $OCH_3$. In various cases, each of $R^a$ and $R^b$ independently is $C_{1-3}$fluoroalkyl, $C_{3-8}$fluorocyloalkyl, $OC_{1-3}$fluoroalkyl, $OC_{3-8}$fluorocyloalkyl, or halo. In some cases, at least one of $R^a$ and $R^b$ is $CF_3$,

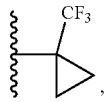

F, or Cl. In various cases, $R^c$, $R^d$, and $R^e$ are each H. In some embodiments, one or more of $R^c$, $R^d$, and $R^e$ is halo, $C_{1-3}$fluoroalkyl, $C_{3-8}$fluorocyloalkyl, $OC_{1-3}$fluoroalkyl, or $OC_{3-8}$fluorocyloalkyl. In some embodiments, one or more of $R^c$, $R^d$, and $R^e$ is F, Cl, $CF_3$ or

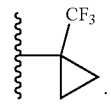

Specifically contemplated compounds of the disclosure include a compound listed in Table A, or a pharmaceutically acceptable salt thereof. In some embodiments, provided herein is a compound or salt thereof selected from the group consisting of A1, A2, A3, A4, A5, and A6. In some cases, the disclosure provides a compound or salt thereof having a structure:

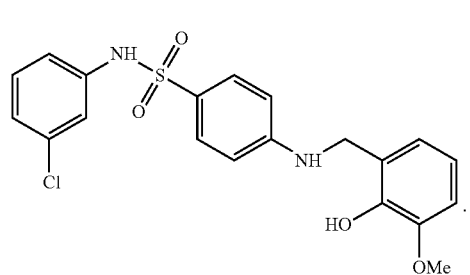

A1

The disclosure also provides a pharmaceutical composition comprising a compound described herein and a pharmaceutically acceptable carrier.

The disclosure further provides a method of inhibiting (S)-Lipoxygenase ("12-LOX") activation in a cell comprising contacting the cell with a compound or composition described herein in an amount effective to inhibit 12-LOX activation.

The disclosure still further another aspect of the disclosure provides a method of inhibiting platelet factor 4 ("PF4") release in cell comprising contacting the cell with a compound or composition described herein in an amount effective to inhibit PF4 release.

The disclosure also provides a method of inhibiting PF4-heparin complex formation in cell comprising contacting the cell with a compound or composition described herein in an amount effective to inhibit PF4-heparin complex formation.

The disclosure further provides a method of inhibiting platelet activation in a cell comprising contacting the cell with a compound or composition described herein in an amount effective to inhibit platelet activation. In some embodiments, the platelet activation is FcγRIIa-mediated platelet activation.

The disclosure still further provides a method of inhibiting thrombin, protease-activated receptor-4 ("PAR4"), and/or glycoprotein VI ("GPVI") signaling in a cell comprising contacting the cell with a compound or composition described herein in an amount effective to inhibit PAR4 and/or GPVI signaling.

This disclosure also provides a method of treating a thrombotic disorder in a subject in need thereof comprising administering to the subject a therapeutically effective amount of a compound or composition described herein. Examples of the thrombotic disorder include arterial thrombosis, deep vein thrombosis ("DVT"), pulmonary embolism ("PE"), ischemic stroke, immune thrombocytopenia ("ITP"), Heparin-induced thrombocytopenia ("HIT"), and Heparin-induced thrombocytopenia and thrombosis ("HITT").

Also provided herein is a method of preventing thrombosis in a subject comprising administering to the subject a therapeutically effective amount of a compound or composition described herein.

Further provided herein is a method of treating thrombocytopenia in a subject in need thereof comprising administering to the subject a therapeutically effective amount of a compound or composition described herein.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1:
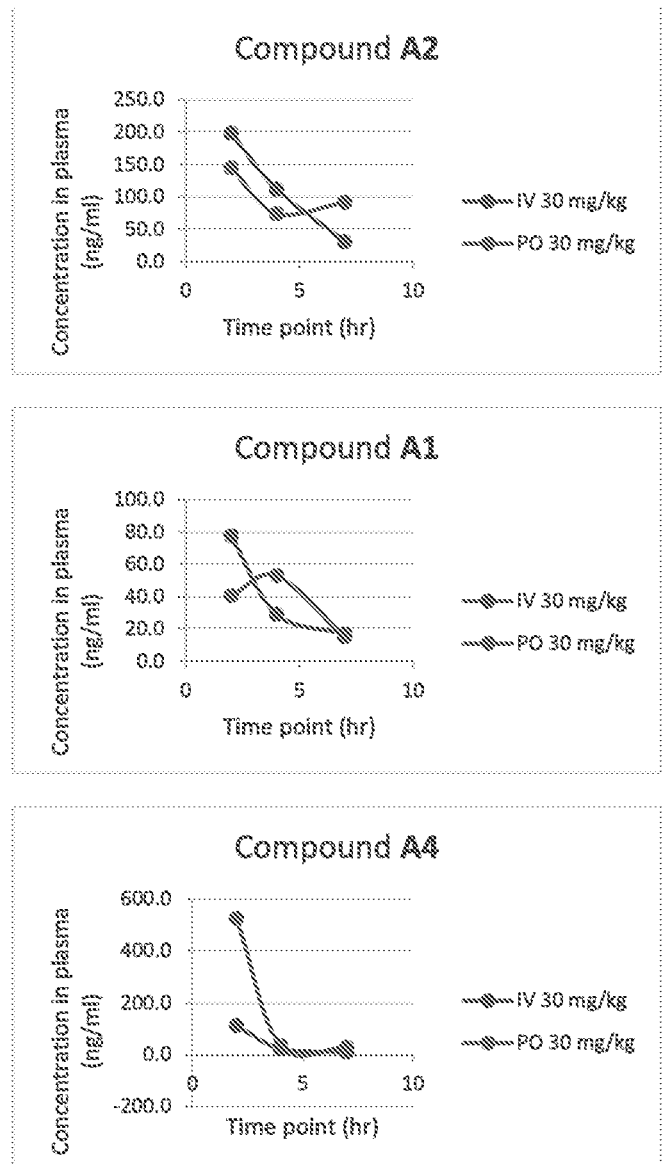
FIG. 1 depicts the concentration of oral- or IV-administered compounds A1, A2, and A4 (30 mg/kg) in the plasma of mice (n=3), monitored at 3 time points (2 h, 4 h, and 7 h), as further described in the Examples section.

Disclosed herein are compounds having a structure of Formula (I):

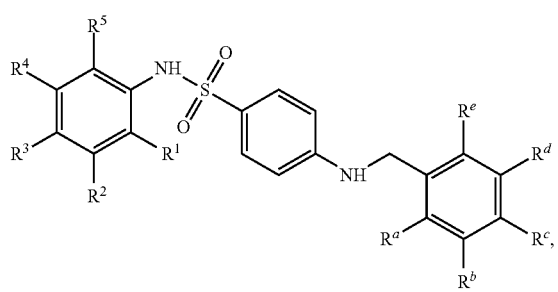

(I)

or pharmaceutically acceptable salts thereof, which can inhibit 12(S)-Lipoxygenase ("12-LOX"), and are useful in treating and preventing diseases relating to platelet hemostasis and thrombosis. The compounds disclosed herein exhibit improved in vivo solubility and potency over ML355 (e.g., at least 10-fold more potent than ML355), without causing bleeding.

The compounds disclosed herein can dose-dependently inhibit human platelet aggregation and 12-LOX oxylipin production. Oral administration of the compounds disclosed herein in mice showed reasonable plasma drug levels by pharmacokinetic assessment. Also, the compounds disclosed herein can impair thrombus growth and vessel occlusion in $FeCl_3$-induced mesenteric, laser-induced cremaster arteriole thrombosis, and immune-mediated anti-GPIX in vivo models in mice. Importantly, hemostatic plug formation and bleeding after treatment with the compounds described herein was minimal in mice in response to laser ablation on the saphenous vein or in a cremaster microvasculature laser-induced rupture model.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. For example, an alkyl group can be substituted with one or more fluorine atoms to form a fluoroalkyl group (e.g., a methyl group can be substituted with 1 to 3 fluorine atoms to provide $CH_2F$, $CHF_2$, or $CF_3$).

As used herein, the term "cycloalkyl" refers to a monovalent aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (e.g., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to eight carbon atoms. Unless otherwise indicated, cycloalkyl groups can be substituted or unsubstituted, e.g., optionally substituted with, for example, one to three groups, independently selected alkyl, alkylene-OH, $C(O)NH_2$, $NH_2$, oxo (=O), aryl, haloalkyl, halo, and OH. In some cases, the cycloalkyl group can be substituted with one or more (e.g., 1 to 3) fluoro groups.

As used herein, the term "halo" refers to a fluoro, chloro, bromo, or iodo group. The term "haloalkyl" refers to an alkyl group that is substituted with at least one (e.g., 1, 2, 3, 4, 5, or 1-5, or 1-3) halogen. "Fluoroalkyl" refers to a haloalkyl group wherein the halo is fluoro.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject includes males and females.

As used herein the terms "treating", "treat" or "treatment" and the like include preventative (e.g., prophylactic) and palliative treatment. In some cases, the treating refers to treating a symptom of a disorder or disease as disclosed herein.

Compounds

Provided herein are compounds of Formula (I), or pharmaceutically acceptable salts thereof:

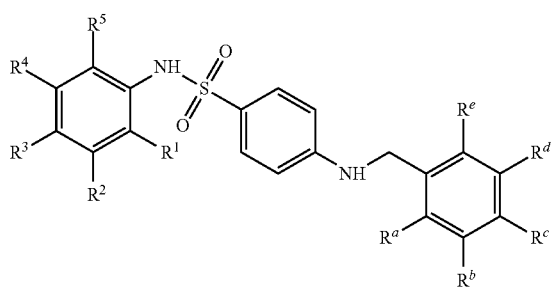

(I)

wherein:
$R^2$ is halo, $C_{1-3}$fluoroalkyl, $C_{3-8}$fluorocyloalkyl, $OC_{1-3}$fluoroalkyl, or $OC_{3-8}$fluorocyloalkyl;
each of $R^1$, $R^3$, $R^4$, and $R^5$ independently is H, halo, $C_{1-3}$fluoroalkyl, $C_{3-8}$fluorocyloalkyl, $OC_{1-3}$fluoroalkyl, or $OC_{3-8}$fluorocyloalkyl;
each of $R^a$ and $R^b$ independently is OH, $OC_{1-3}$alkyl, $C_{1-3}$fluoroalkyl, $C_{3-8}$fluorocyloalkyl, $OC_{1-3}$fluoroalkyl, $OC_{3-8}$fluorocyloalkyl, or halo; and
each of $R^c$, $R^d$, and $R^e$ independently is H, OH, $OC_{1-3}$alkyl, $C_{1-3}$fluoroalkyl, $C_{3-8}$fluorocyloalkyl, $OC_{1-3}$fluoroalkyl, $OC_{3-8}$fluorocyloalkyl, or halo.

In some embodiments, $R^2$ is halo (e.g., Br, Cl, or F). In various embodiments, $R^2$ is Cl or F. In some cases, $R^2$ is Cl. In various cases, $R^2$ is $C_{1-3}$fluoroalkyl (e.g., $CH_2F$, $CHF_2$, or $CF_3$), $C_{3-8}$fluorocyloalkyl (e.g., cyclopropyl, cyclobutyl, cyclopentyl, or cyclohexyl substituted with F, $CH_2F$, $CHF_2$, or $CF_3$), $OC_{1-3}$fluoroalkyl, or $OC_{3-8}$fluorocyloalkyl. In some embodiments, $R^2$ is $CF_3$ or

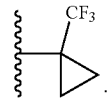

In some cases, each of $R^1$, $R^3$, $R^4$, and $R^5$ is H. In various cases, one or more of $R^1$, $R^3$, $R^4$, and $R^5$ is halo (e.g., Br, Cl, or F), $C_{1-3}$fluoroalkyl (e.g., $CH_2F$, $CHF_2$, or $CF_3$), $C_{3-8}$fluorocyloalkyl (e.g., cyclopropyl, cyclobutyl, cyclopentyl, or cyclohexyl substituted with F, $CH_2F$, $CHF_2$, or $CF_3$), $OC_{1-3}$fluoroalkyl, or $OC_{3-8}$fluorocyloalkyl. In some embodiments, one or more of $R^1$, $R^3$, $R^4$, and $R^5$ is F, Cl, $CF_3$ or

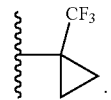

In various embodiments, $R^1$ is H or F; $R^2$ is Cl, $CF_3$, or

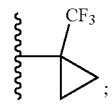

;

$R^3$ is H or F; $R^4$ is H; and $R^5$ is H.

In some cases, each of $R^a$ and $R^b$ independently is OH or $OC_{1-3}$alkyl. In various cases, one of $R^a$ and $R^b$ is OH or $OC_{1-3}$alkyl; and the other of $R^a$ and $R^b$ is $C_{1-3}$fluoroalkyl, $C_{3-8}$fluorocyloalkyl, $OC_{1-3}$fluoroalkyl, $OC_{3-8}$fluorocyloalkyl, or halo. In some embodiments, $OC_{1-3}$alkyl is $OCH_3$. In various embodiments, each of $R^a$ and $R^b$ independently is $C_{1-3}$fluoroalkyl, $C_{3-8}$fluorocyloalkyl, $OC_{1-3}$fluoroalkyl, $OC_{3-8}$fluorocyloalkyl, or halo. In some cases, at least one of $R^a$ and $R^b$ is $CF_3$,

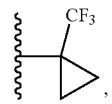

,

F, or Cl. In various cases, $R^c$, $R^d$, and $R^e$ are each H. In some embodiments, one or more of $R^c$, $R^d$, and $R^e$ is halo, $C_{1-3}$fluoroalkyl, $C_{3-8}$fluorocyloalkyl, $OC_{1-3}$fluoroalkyl, or $OC_{3-8}$fluorocyloalkyl. In some embodiments, one or more of $R^c$, $R^d$, and $R^e$ is F, Cl, $CF_3$ or

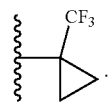

Specifically contemplated compounds of the disclosure include a compound listed in Table A, or a pharmaceutically acceptable salt thereof:

TABLE A

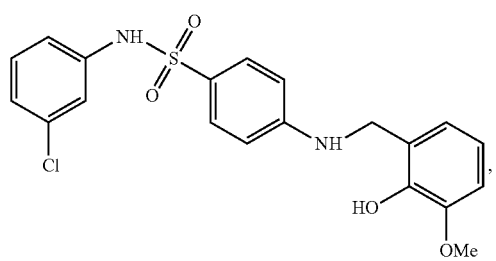
A1

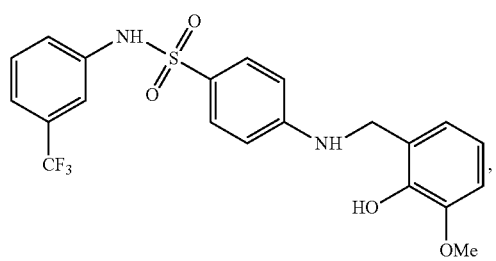 [SMILES: COc1cccc(CNc2ccc(S(=O)(=O)Nc3cccc(Cl)c3)cc2)c1O]
A2

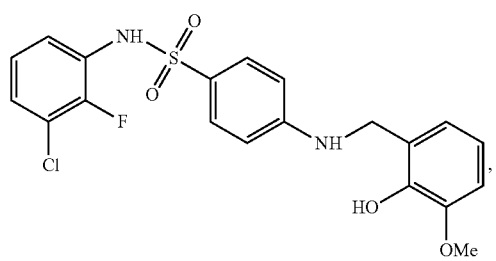 [SMILES: COc1cccc(CNc2ccc(S(=O)(=O)Nc3cccc(Cl)c3F)cc2)c1O]
A3

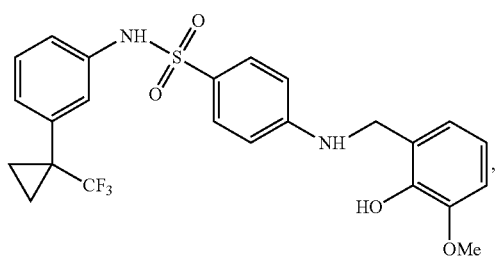 [SMILES: COc1cccc(CNc2ccc(S(=O)(=O)Nc3cccc(C4(C(F)(F)F)CC4)c3)cc2)c1O]
A4

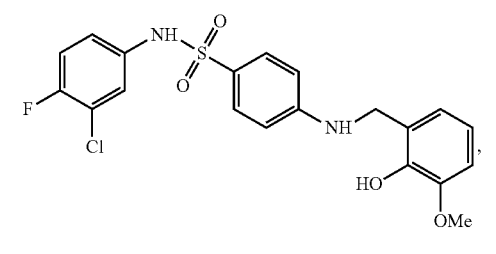 [SMILES: COc1cccc(CNc2ccc(S(=O)(=O)Nc3ccc(F)c(Cl)c3)cc2)c1O]
A5

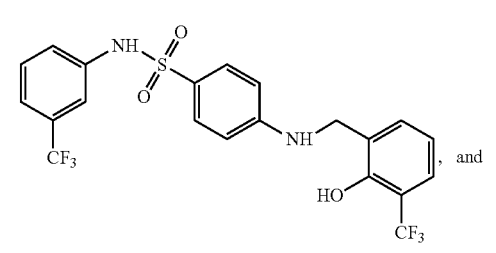 [SMILES: O=S(=O)(Nc1cccc(C(F)(F)F)c1)c1ccc(NCc2cccc(C(F)(F)F)c2O)cc1]
A6, and

TABLE A-continued

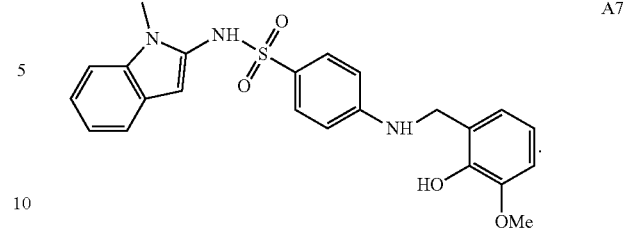
A7

In some embodiments, provided herein is a compound or salt thereof selected from the group consisting of A1, A2, A3, A4, A5, and A6. In some cases, the disclosure provides a compound or salt thereof having a structure:

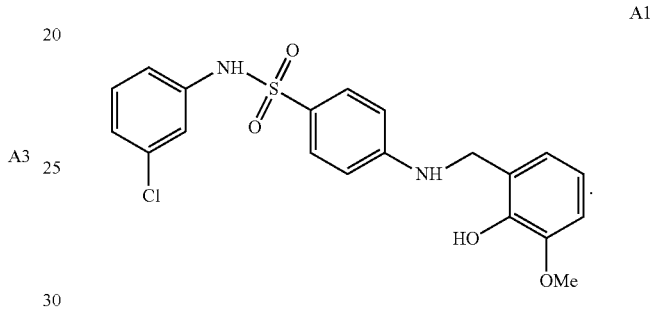
A1

Compound Synthesis

The compounds provided herein can be synthesized using conventional techniques and readily available starting materials known to those skilled in the art. In general, the compounds provided herein are conveniently obtained via standard organic chemistry synthesis methods.

For example, compounds having a meta-chloro aniline group can be synthesized by reacting an appropriate 3-chloroaniline with 4-nitrobenzesulfonyl chloride to form a desired N-(3-chlorophenyl)-4-nitrobenzenesulfonamide compound, reducing the nitro group to an amino group, and then reacting the amino group with an appropriate benzaldehyde group to form the desired compound, as shown in Scheme 1 in the Examples section.

Compounds that have other substitution patterns can be synthesized by reacting 4-aminobenzenesulfonamide with an appropriate benzaldehyde group to form a 4-(benzyl) aminobenzenesulfamide compound, and coupling the compound with an appropriate arylbromide group, to result in the desired compound, as shown in Scheme 2 in the Examples section.

Additional synthetic procedures for preparing the inhibitors disclosed herein can be found in the Examples section.

Methods of Use

Adequate platelet reactivity is required for maintaining hemostasis. However, excessive platelet reactivity can also lead to the formation of occlusive thrombi. Platelet 12(S)-lipoxygenase ("12-LOX"), an oxygenase highly expressed in the platelet, has been demonstrated to regulate platelet function and thrombosis ex vivo, supporting a key role for 12-LOX in the regulation of in vivo thrombosis. It has been found that the compounds described herein (e.g., the compounds of Formula (I), the compounds listed in Table A, and pharmaceutically acceptable salts of the foregoing) are able to target 12-LOX in vivo, which has implications on thrombosis and hemostasis. Thus, provided herein is a method of inhibiting 12-LOX in a cell comprising contacting the cell with a compound disclosed herein (e.g., a compound of Formula (I), a compound listed in Table A, or pharmaceutically acceptable salts of the foregoing), in an amount effective to inhibit 12-LOX activation. In some embodiments, the contacting is in vivo. In various embodiments, the contacting is in vitro.

12-LOX has been shown to attenuate thrombin PAR4-, and GPVI-mediated signalizing pathways in human platelet activation. Therefore, also provided herein is a method of inhibiting thrombin, PAR4- and/or GPVI-signaling in a cell comprising contacting the cell with a compound disclosed herein (e.g., a compound of Formula (I), a compound listed in Table A, or pharmaceutically acceptable salts of the foregoing), in an amount effective to inhibit PAR4 and/or GPVI signaling. Further, pharmacological inhibition of 12-LOX by the compounds described herein can attenuate platelet activation, such as FcγRIIa-mediated platelet activation. Therefore, also disclosed herein is a method of inhibiting platelet activation in a cell, such as FcγRIIa-mediated platelet activation, comprising contacting the cell with a compound disclosed herein (e.g., a compound of Formula (I), a compound listed in Table A, or pharmaceutically acceptable salts thereof), in an amount effective to inhibit platelet activation. In some embodiments, the contacting is in vivo. In various embodiments, the contacting is in vitro.

The compounds disclosed herein (e.g., a compound of Formula (I), a compound listed in Table A, or pharmaceutically acceptable salts of the foregoing) also can prevent the release of platelet factor 4 ("PF4") and formation of PF4-heparin complex in a cell. Thus, also provided herein are methods of inhibiting PF4 release and/or PF4-heparin complex formation in cell comprising contacting the cell with a compound disclosed herein (e.g., a compound of Formula (I), a compound listed in Table A, or pharmaceutically acceptable salts of the foregoing), in an amount effective to inhibit PF4 release and/or PF4-heparin complex formation. In some embodiments, the contacting is in vivo. In various embodiments, the contacting is in vitro.

Also provided herein is administration of a therapeutically effective amount of a compound disclosed herein (e.g., a compound of Formula (I), a compound listed in Table A, or pharmaceutically acceptable salts of the foregoing) to subject in need thereof. The ability of the compounds disclosed herein to inhibit platelet activation, thrombocyptopenia, and/or thrombus formation in a subject in need thereof provides therapeutic efficacy in treating a wide range of thrombotic disorders. Particularly contemplated thrombotic disorders that can be treated or prevented via administration of a compound disclosed herein include arterial thrombosis, deep vein thrombosis ("DVT"), pulmonary embolism ("PE"), ischemic stroke, immune thrombocytopenia ("ITP"), Heparin-induced thrombocytopenia ("HIT"), and Heparin-induced thrombocytopenia and thrombosis ("HITT"). Further provided herein are methods of preventing thrombosis and/or treating thrombocytopenia in a subject comprising administering to the subject a therapeutically effective amount of a compound disclosed herein (e.g., a compound of Formula (I), a compound listed in Table A, or pharmaceutically acceptable salts of the foregoing), in an amount effect to prevent thrombosis and/or treat thrombocytopenia in the subject.

Further guidance for using compounds disclosed herein for inhibiting 12-LOX, such as a compound of Formula (I), a compound listed in Table A, or pharmaceutically acceptable salts of the foregoing, can be found in the Examples section, below.

Pharmaceutical Formulations, Dosing, and Routes of Administration

The methods provided herein include the manufacture and/or use of pharmaceutical compositions, which include one or more of the compounds provided herein. Also included are the pharmaceutical compositions themselves. Pharmaceutical compositions typically include a pharmaceutically acceptable carrier. Thus, provided herein are pharmaceutical formulations that include a compound described herein (e.g., a compound of Formula (I), a compound listed in Table A, or a pharmaceutically acceptable salt of the foregoing), as previously described herein, and one or more pharmaceutically acceptable carriers.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. See, for example, Berge et al. (1977) "Pharmaceutical Salts", *J. Pharm. Sci.* 66: 1-19.

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Scheme 1. General Scheme for meta-Chloro Compounds

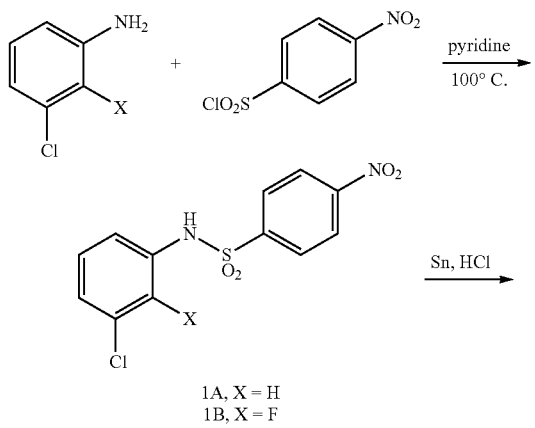

1A, X = H
1B, X = F

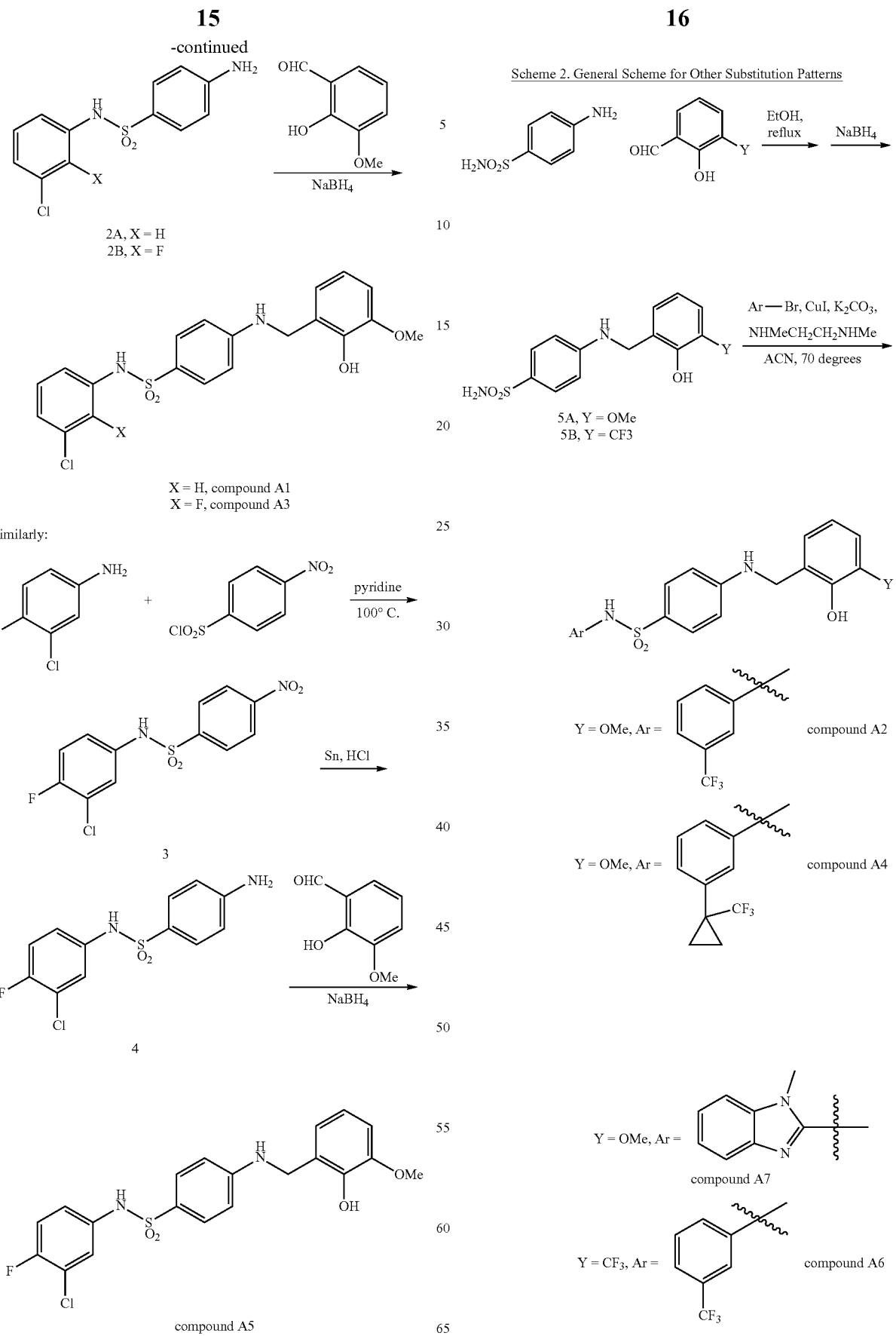

Synthesis of N-(3-chlorophenyl)-4-((2-hydroxy-3-methoxybenzyl)amino) benzenesulfonamide (A1)

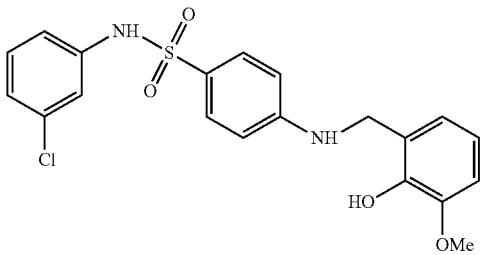 [SMILES: COc1cccc(CNc2ccc(S(=O)(=O)Nc3cccc(Cl)c3)cc2)c1O]

A solution of 4-amino-N-(3-chlorophenyl)benzenesulfonamide (2A) (Zheng et al, *Biorganic and Medicinal Chemistry* 2007, 15, 1014-1021) (0.20 g, 0.71 mmol) in ethanol (5 mL) was treated with ortho-vanillin (0.14 g, 0.92 mmol). The resulting suspension was refluxed for 8 hours. The mixture was cooled to room temperature, treated cautiously with sodium borohydride (67 mg, 1.8 mmol), and stirred at room temperature overnight. The mixture was treated with methanol and water and stirred for 1.5 hours. The solids were filtered and washed well with ethanol and dichloromethane, and the filtrate was concentrated to give an oil. This residue was purified via silica gel chromatography, eluting with 5% methanol in dichloromethane, to give 0.071 g of the title compound. $^1$H NMR (400 MHz, Methanol-d4) δ 7.47-7.38 (m, 2H), 7.18-7.04 (m, 2H), 6.97 (dddd, J=7.8, 5.7, 2.1, 1.0 Hz, 2H), 6.78 (ddd, J=14.1, 7.8, 1.7 Hz, 2H), 6.69 (t, J=7.8 Hz, 1H), 6.60-6.49 (m, 2H), 4.30 (s, 2H), 3.83 (s, 3H). HRMS: measured, m/z=419.0825 (predicted m/z=419.0827). HPLC: 93.6% (retention time, 6.89 minutes @ 250 nm wavelength. Mobile phase: 90:10 water:acetonitrile→90:10 acetonitrile:water over 13 minutes, with 0.1% TFA added to both water and ACN.)

Synthesis of 4-((2-hydroxy-3-methoxybenzynamino)-N-(3-(trifluoromethyl)phenyl) benzenesulfonamide (A2)

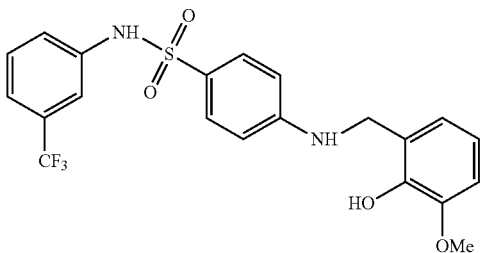 [SMILES: COc1cccc(CNc2ccc(S(=O)(=O)Nc3cccc(C(F)(F)F)c3)cc2)c1O]

A mixture of 4-((2-hydroxy-3-methoxybenzyl)amino) benzenesulfonamide (5A) (Luci et al, *Journal of Medicinal Chemistry* 2014, 57(2), 495-506) (0.22 g, 0.73 mmol), 1-bromo-3-(trifluoromethyl)benzene (0.20 g, 0.88 mmol), N,N-dimethylethylenediamine (0.032 g, 0.37 mmol), potassium carbonate (0.25 g, 1.8 mmol), copper(I) iodide (7.0 mg, 0.037 mmol), and acetonitrile (7 mL) in a sealed tube was degassed with nitrogen (for 15 minutes) and then heated to 70° C. for 24 hours. The mixture was cooled to room temperature and treated with saturated aqueous ammonium chloride (40 mL). The dark blue solution was extracted with ethyl acetate until the organic layer was clear (3×30 mL). The combined organic extracts were washed with water (25 mL) and brine (25 mL), dried over magnesium sulfate, and concentrated to give an oil. The crude product was purified via silica gel chromatography, eluting with 4% methanol in dichloromethane, to give 0.117 g of the title compound. $^1$H NMR (400 MHz, Methanol-d4) δ 7.50-7.40 (m, 2H), 7.40-7.21 (m, 4H), 6.82-6.73 (m, 2H), 6.67 (t, J=7.8 Hz, 1H), 6.61-6.49 (m, 2H), 4.29 (s, 2H), 3.81 (s, 3H). HPLC: 100% (retention time, 6.97 minutes @ 250 nm wavelength. Mobile phase: 90:10 water:acetonitrile→90:10 acetonitrile:water over 13 minutes, with 0.1% TFA added to both water and ACN.) HRMS: measured m/z=453.1089 [M+H]+ (predicted m/z=453.1090).

Synthesis of N-(3-chloro-2-fluorophenyl)-4-((2-hydroxy-3-methoxybenzyl)amino) benzenesulfonamide (A3)

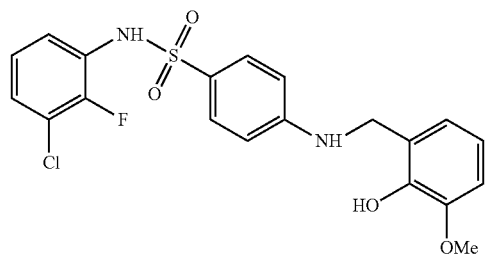 [SMILES: COc1cccc(CNc2ccc(S(=O)(=O)Nc3cccc(Cl)c3F)cc2)c1O]

A solution of 3-chloro-2-fluoroaniline (0.50 g, 3.4 mmol) in pyridine (2 mL) was treated with 3 equal portions of 4-nitrobenzenesulfonyl chloride (0.84 g, 3.8 mmol). The resulting mixture was heated at 100° C. for 3 hours and then cooled to room temperature. The reaction mixture was acidified with 2 N HCl and extracted with ethyl acetate (3×25 mL). The combined extracts were washed with water and brine, dried over magnesium sulfate, and concentrated to give an oil. The residue was taken up in hexane and re-concentrated to give an off-white powder that was suspended in 1:10 ethyl acetate:hexane and ground. The solids were filtered away, washed well with hexane, and air-dried to give 0.99 g of N-(3-chloro-2-fluoro-phenyl)-4-nitrobenzenesulfonamide (1B). $^1$H NMR (400 MHz, DMSO-d6) δ 10.82 (s, 1H), 8.44-8.34 (m, 2H), 8.03-7.94 (m, 2H), 7.42 (td, J=7.4, 6.9, 2.3 Hz, 1H), 7.26-7.08 (m, 2H).

A solution of N-(3-chloro-2-fluoro-phenyl)-4-nitrobenzenesulfonamide (1B) (0.95 g, 2.9 mmol) in THF (10 mL) was treated with tin (1.2 g, 10 mmol) and concentrated HCl (4.3 mL), in that order; the HCl was added gradually over 4 minutes. The resulting suspension was refluxed for 2.5 hours and then cooled to room temperature. The mixture was made basic with the dropwise addition of 2 N NaOH. The suspension that formed was filtered through Celite; the Celite cake was washed well with water and ethyl acetate. The filtrate was transferred to a separatory funnel, where the aqueous layer was separated and re-extracted with ethyl acetate (50 mL). The organic extracts were combined, washed with water (50 mL) and brine (50 mL), and dried over magnesium sulfate. Concentration gave a semi-solid that was triturated with ether to give 0.39 g of 4-amino-N-(3-chloro-2-fluoro-phenyl)benzenesulfonamide (2B) as a solid. $^1$H NMR (400 MHz, DMSO-d6) δ 9.92 (s, 1H), 7.34 (d, J=8.6 Hz, 2H), 7.28 (td, J=7.4, 6.6, 1.6 Hz, 1H), 7.19 (td, J=7.7, 7.1, 1.7 Hz, 1H), 7.10 (td, J=8.1, 1.4 Hz, 1H), 6.57-6.48 (m, 2H), 6.02 (s, 2H).

A solution of 4-amino-N-(3-chloro-2-fluoro-phenyl)benzenesulfonamide (2B) (0.19 g, 0.63 mmol) in ethanol (5 mL) was treated with ortho-vanillin (0.14 g, 0.94 mmol). The resulting suspension was refluxed for 24 hours and then cooled to room temperature. The reaction mixture was treated cautiously with sodium borohydride (0.071 g, 1.9 mmol), stirred at room temperature overnight, treated with methanol and water, and stirred for 30 minutes. The solids were filtered through Celite, and the Celite cake was washed well with ethanol and dichloromethane. The filtrate was concentrated to give an oil. This residue was purified via silica gel chromatography, eluting with 5% methanol in dichloromethane, to give 0.101 g of the title compound. $^1$H NMR (400 MHz, DMSO-d$_6$) δ 9.92 (s, 1H), 8.72 (s, 1H), 7.37 (d, J=8.8 Hz, 2H), 7.26 (t, J=7.3 Hz, 1H), 7.18 (t, J=7.3 Hz, 1H), 7.08 (dd, J=8.8, 7.5 Hz, 1H), 6.95 (t, J=5.8 Hz, 1H), 6.87-6.79 (m, 1H), 6.76-6.65 (m, 2H), 6.56 (d, J=8.9 Hz, 2H), 4.20 (d, J=5.7 Hz, 2H), 3.77 (s, 3H). HRMS: measured, m/z of [M+H]+=437.0736 (predicted m/z=437.0733). HPLC: 94.8% (retention time, 6.86 minutes @ 250 nm wavelength. Mobile phase: 90:10 water:acetonitrile→90:10 acetonitrile:water over 13 minutes, with 0.1% TFA added to both water and ACN.)

Synthesis of 4-((2-hydroxy-3-methoxybenzyl) amino)-N-(3-(1-(trifluoromethyl) cyclopropyl)phenyl)benzenesulfonamide (A4)

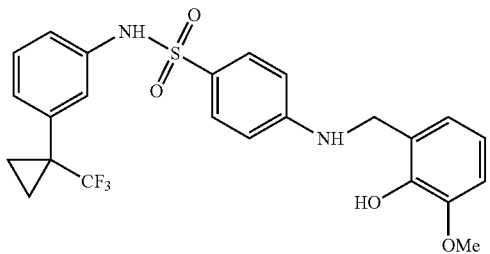 [SMILES: COc1cccc(CNc2ccc(S(=O)(=O)Nc3cccc(C4(C(F)(F)F)CC4)c3)cc2)c1O]

A mixture of 4-((2-hydroxy-3-methoxybenzyl)amino) benzenesulfonamide (5A) (Luci et al, *Journal of Medicinal Chemistry* 2014, 57(2), 495-506) (0.40 g, 1.3 mmol), 1-bromo-3-(1-(trifluoromethyl)cyclopropyl)benzene (0.41 g, 1.6 mmol), N,N-dimethylethylenediamine (0.057 g, 0.65 mmol), potassium carbonate (0.45 g, 3.2 mmol), copper(I) iodide (12 mg, 0.065 mmol), and dioxane (5 mL) in a sealed tube was degassed with nitrogen (for 10 minutes) and then heated to 80° C. for 2 days. The mixture was cooled to room temperature and treated with saturated aqueous ammonium chloride (50 mL). The dark solution was extracted with dichloromethane (4×40 mL). The combined organic extracts were washed with water (50 mL) and brine (50 mL), dried over magnesium sulfate, and concentrated to give an oil. The crude product was purified via silica gel chromatography, eluting with 4% methanol in dichloromethane, to give 0.091 g of the title compound. $^1$H NMR (400 MHz, Methanol-d4) δ 7.44-7.34 (m, 2H), 7.22-7.10 (m, 3H), 7.02 (ddd, J=7.8, 2.2, 1.3 Hz, 1H), 6.79 (ddd, J=18.8, 7.9, 1.6 Hz, 2H), 6.70 (t, J=7.8 Hz, 1H), 6.59-6.51 (m, 2H), 4.31 (s, 2H), 3.84 (s, 3H), 1.31-1.23 (m, 2H), 0.94-0.83 (m, 2H). Trace of ether. HPLC: 98.9% (retention time, 7.39 minutes @ 250 nm wavelength. Mobile phase: 90:10 water:acetonitrile→90:10 acetonitrile:water over 13 minutes, with 0.1% TFA added to both water and ACN.) HRMS: Measured m/z of [M+H]+ =493.1402 (predicted m/z=493.1403).

Synthesis of N-(3-chloro-4-fluorophenyl)-4-((2-hydroxy-3-methoxybenzyl)amino) benzenesulfonamide (A5)

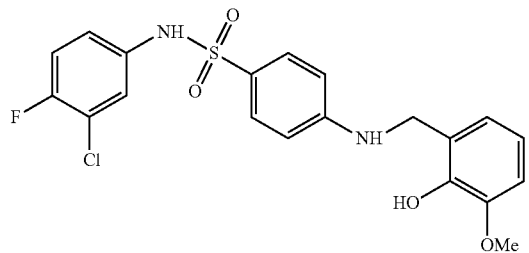 [SMILES: COc1cccc(CNc2ccc(S(=O)(=O)Nc3ccc(F)c(Cl)c3)cc2)c1O]

A solution of 3-chloro-4-fluoroaniline (0.50 g, 3.4 mmol) in pyridine (1.7 mL) was treated with 3 equal portions of 4-nitrobenzenesulfonyl chloride (0.84 g, 3.8 mmol). The resulting mixture was heated at 100° C. for 3.5 hours. The solution was then cooled to room temperature, acidified with 2 N HCl and extracted with ethyl acetate (2×25 mL). The combined extracts were washed with water and brine, dried over magnesium sulfate, and concentrated to give a solid. This material was triturated with 1:10 ethyl acetate:hexane, filtered, and air-dried to give 1.0 g of N-(3-chloro-4-fluorophenyl)-4-nitrobenzenesulfonamide (3). $^1$H NMR (400 MHz, DMSO-d6) δ 10.79 (s, 1H), 8.43-8.31 (m, 2H), 8.04-7.89 (m, 2H), 7.31 (t, J=9.0 Hz, 1H), 7.23 (dd, J=6.5, 2.6 Hz, 1H), 7.05 (ddd, J=8.8, 4.1, 2.6 Hz, 1H).

A solution of N-(3-chloro-4-fluorophenyl)-4-nitrobenzenesulfonamide (3) (1.0 g, 3.0 mmol) in THF (10 mL) was treated with tin (1.3. g, 11 mmol) and concentrated HCl (4.5 mL), in that order; the HCl was added gradually over 4.5 minutes. The resulting suspension was refluxed for 3.5 hours and then stirred at room temperature overnight. The mixture was made basic with the dropwise addition of 2 N NaOH, and the thick suspension that formed was filtered through Celite. The Celite cake was washed well with ethyl acetate, and the filtrate was transferred to a separatory funnel; the aqueous layer was separated and re-extracted with ethyl acetate (3×30 mL). The organic layers were combined, washed with water (2×50 mL) and brine (50 mL), and dried over magnesium sulfate. Concentration gave an oil that solidified upon standing. The crude product was chromatographed over silica gel, eluting with 1:1 hexane:ethyl acetate, to give 0.45 g of 4-amino-N-(3-chloro-4-fluorophenyl)benzenesulfonamide (4). $^1$H NMR (400 MHz, DMSO-d6) δ 10.04 (s, 1H), 7.40-7.33 (m, 2H), 7.27 (t, J=9.1 Hz, 1H), 7.14 (dd, J=6.6, 2.7 Hz, 1H), 7.01 (ddd, J=8.9, 4.2, 2.7 Hz, 1H), 6.56-6.49 (m, 2H), 6.02 (s, 2H).

A solution of 4-amino-N-(3-chloro-4-fluoro-phenyl)benzenesulfonamide (4) (0.23 g, 0.75 mmol) in ethanol (5 mL) was treated with ortho-vanillin (0.17 g, 1.1 mmol); the resulting suspension was refluxed for 24 hours. The suspension was cooled to room temperature, treated cautiously with sodium borohydride (0.085 g, 2.3 mmol), and stirred at room temperature overnight. The mixture was treated with methanol and water and stirred for 30 minutes. The solids were filtered through Celite, and the Celite cake was washed well with ethanol and dichloromethane. The filtrate was concentrated to give an oil. The product was purified via silica gel chromatography, eluting with 2% methanol in dichloromethane, to give 0.93 g of the title compound. ¹H NMR (400 MHz, DMSO-d6) δ 10.07 (s, 1H), 8.76 (s, 1H), 7.39 (s, 2H), 7.26 (t, J=9.1 Hz, 1H), 7.14 (dd, J=6.6, 2.6 Hz, 1H), 7.08-6.91 (m, 2H), 6.83 (dd, J=7.6, 1.9 Hz, 1H), 6.76-6.60 (m, 2H), 6.56 (d, J=8.7 Hz, 2H), 4.19 (d, J=5.8 Hz, 2H), 3.77 (s, 3H). HPLC: 98.3% (retention time, 7.13 minutes @ 250 nm wavelength. Mobile phase: 90:10 water:acetonitrile→90:10 acetonitrile:water over 13 minutes, with 0.1% TFA added to both water and ACN.) HRMS: Measured m/z of [M+H]+=437.0728 (predicted m/z=437.0733).

Synthesis of 4-((2-hydroxy-3-(trifluoromethyl)benzyl)amino)-N-(3-(trifluoromethyl)phenyl)benzenesulfonamide (A6)

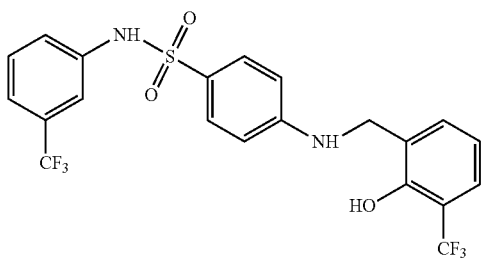 [SMILES: O=S(=O)(Nc1cccc(C(F)(F)F)c1)c1ccc(NCc2cccc(C(F)(F)F)c2O)cc1]

A solution of 4-aminobenzenesulfonamide (0.40 g, 2.3 mmol), 2-hydroxy-3-(trifluoromethyl)benzaldehyde (Filippova et al, *Tetrahedron* 2016, 72(41), 6572-6577) (0.51 g, 2.7 mmol), and ethanol (10 mL) was refluxed overnight and then cooled to room temperature. The resulting suspension was treated with sodium borohydride (0.13 g, 3.5 mmol) and was stirred at room temperature overnight. The solution was concentrated, and the residue was partitioned between water and dichloromethane. The aqueous layer was separated and extracted with ethyl acetate (3×25 mL). The combined organic extracts were dried over magnesium sulfate and concentrated. This material was purified via silica gel chromatography, eluting with 5% methanol in dichloromethane, to give 0.25 g of 4-((2-hydroxy-3-methoxybenzyl)amino) benzenesulfonamide (5B). ¹H NMR (400 MHz, Methanol-d4) δ 7.66-7.58 (m, 2H), 7.43 (dd, J=7.3, 5.5 Hz, 2H), 6.93 (t, J=7.7 Hz, 1H), 6.70-6.65 (m, 2H), 4.43 (s, 2H).

A mixture of 4-((2-hydroxy-3-(trifluoromethyl)benzyl)amino)benzenesulfonamide (5B) (0.12 g, 0.36 mmol), 1-bromo-3-(trifluoromethyl)benzene (0.097 g, 0.43 mmol), N,N-dimethylethylenediamine (16 mg, 0.18 mmol), potassium carbonate (0.13 g, 0.90 mmol), copper(I) iodide (3 mg, 0.018 mmol), and acetonitrile (5 mL) in a sealed tube was degassed with nitrogen (for 10 minutes) and then heated to 70° C. for 24 hours. The mixture was cooled to room temperature and treated with saturated aqueous ammonium chloride (30 mL). The dark blue solution was extracted with ethyl acetate until the organic layer was clear (3×30 mL). The combined organic extracts were washed with water (25 mL) and brine (25 mL), dried over magnesium sulfate, and concentrated to give an oil. The crude product was purified via prep TLC, eluting with 4% methanol in dichloromethane, to give 0.060 g of the title compound. ¹H NMR (400 MHz, DMSO-d6) δ 10.35 (s, 1H), 9.59 (s, 1H), 7.44 (dd, J=12.3, 8.3 Hz, 4H), 7.31 (d, J=13.6 Hz, 4H), 7.01 (s, 1H), 6.92 (t, J=7.8 Hz, 1H), 6.58 (d, J=8.7 Hz, 2H), 4.31 (d, J=5.4 Hz, 2H). HPLC: 94.2% (retention time, 7.54 minutes @ 250 nm wavelength. Mobile phase: 90:10 water:acetonitrile→90:10 acetonitrile:water over 13 minutes, with 0.1% TFA added to both water and ACN.) HRMS: measured m/z=491.0859 [M+H]+(predicted m/z=491.0859).

Synthesis of 4-((2-hydroxy-3-methoxybenzynamino)-N-(1-methyl-1H-indol-2-yl)benzenesulfonamide (A7)

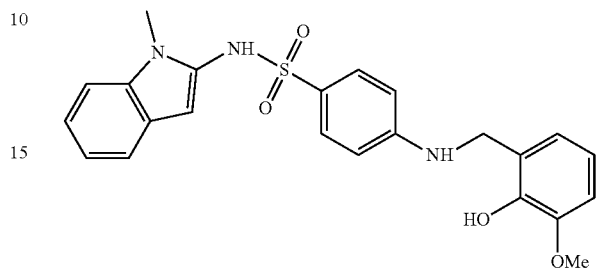

A mixture of 4-((2-hydroxy-3-methoxybenzyl)amino) benzenesulfonamide (5A)² (Luci et al, *Journal of Medicinal Chemistry* 2014, 57(2), 495-506) (0.40 g, 1.3 mmol) (0.40 g, 1.3. mmol), 2-bromo-1-methylbenzimidazole (0.33 g, 1.6 mmol), N,N-dimethylethylenediamine (0.057 g, 0.65 mmol), potassium carbonate (0.45 g, 3.2 mmol), copper(I) iodide (12 mg, 0.065 mmol), and dioxane (5 mL) in a sealed tube was degassed with nitrogen (for 10 minutes) and then heated to 80° C. for 3 days. The mixture was cooled to room temperature and treated with saturated aqueous ammonium chloride (50 mL). The solution was extracted with dichloromethane (5×40 mL). The combined organic extracts were washed with water (50 mL) and brine (50 mL), dried over magnesium sulfate, and concentrated. The residue was triturated with ethyl acetate, and the solids that formed were filtered and washed well with ethyl acetate. The filtrate was concentrated, and this residue was purified via silica gel chromatography, eluting with 5% methanol in dichloromethane. Yield: 0.11 g of the title compound. ¹H NMR (400 MHz, DMSO-d6) δ 11.61 (s, 1H), 8.73 (s, 1H), 7.56 (d, J=8.6 Hz, 2H), 7.42-7.29 (m, 2H), 7.14 (ddd, J=7.3, 5.2, 1.5 Hz, 2H), 6.86-6.77 (m, 1H), 6.74 (dd, J=9.0, 7.0 Hz, 2H), 6.66 (t, J=7.8 Hz, 1H), 6.54 (d, J=8.6 Hz, 2H), 4.20 (d, J=5.8 Hz, 2H), 3.76 (s, 3H), 3.38 (s, 3H). HRMS: Measured m/z of [M+H]+=439.1437 (predicted m/z=439.1435).

Pharmacokinetic Study of the Inhibitors in Mice Blood Plasma

The blood plasma concentration of compounds A1, A2, and A4 in mice was determined following per os, oral compound administration ("PO") and intravenous ("IV") administration Specificity. The chromatograms of blank plasma and the blank plasma/spiked with internal standard (CE302) showed that the blank plasma has no significant interference to compounds A1, A2, and A4 and IS determination.

Calibration curve. The concentration range was evaluated from 2.5-5000 ng/ml for compound A2, 1-5000 ng/ml for compound A4, and 5-5000 ng/ml for compound A1. The curve was built with linear regression with weighing (1/X2). The linear regression analysis was performed by plotting the peak area ratio (y) against the concentration (x) in ng/mL. The linearity of the relationship between peak area ratio and concentration was demonstrated by the correlation coefficients (R) obtained for the linear regression.

Instrument Conditions. The LC-MS and mass spectrometry conditions for the compounds tested are shown below.

Chromatographic Conditions:

| | |
|---|---|
| Column: | 5 cm × 2.1 mm I.D., packed with 1.7 μm Aquity BEH C18 (Waters) |
| Mobile Phase A: | 0.1% formic acid in purified deionized water |
| Mobile Phase B: | 0.1% formic acid in acetonitrile |
| Flow Rate: | 0.4 mL/min |
| Injection Volume: | 5 μL |
| Run Time: | 4.5 min |

Gradient Program:

| Time | % A | % B |
|---|---|---|
| 0.01 | 95 | 5 |
| 0.30 | 95 | 5 |
| 0.80 | 1 | 99 |
| 2.50 | 1 | 99 |
| 2.51 | 95 | 5 |
| 4.50 | 95 | 5 |

Mass Spectrometry Conditions:

| Compound | Formula/ Mass. | Precursor ion (m/z) | Product ion (m/z) | Dwell (secs) | Cone Voltage | Col. Energy |
|---|---|---|---|---|---|---|
| A2 | 452 | 452.941 | 136.96 | 0.01 | 20 | 16 |
| A4 | 492 | 492.974 | 136.959 | 0.01 | 26 | 18 |
| A1 | 418 | 416.916 | 281.045 | 0.01 | 38 | 14 |
| CE302 | 454 | 455.16 | 425.2 | 0.01 | 76 | 31 |

Results. The individual and average compound A1, A2, and A4 concentration-time data for IV and PO dosed groups are listed in Table 1, and graphically presented in FIG. 1.

TABLE 1

Compound A1, A2, and A4 Concentration in Mouse Plasma following PO and IV administration at 2, 4, and 7 hours.

| | Compound A2 Concentration in Plasma (ng/ml) | | | | |
|---|---|---|---|---|---|
| | Time point (h) | Mouse 1 | Mouse 2 | Mouse 3 | Mean | SD |
| IV (30 mg/kg) | 2 | 144.3 | 333.3 | 118.1 | 198.6 | 117.4 |
| | 4 | 127.4 | *1369.6 | 96.0 | 111.7 | 22.2 |
| | 7 | 49.3 | 16.4 | 27.4 | 31.0 | 16.8 |

| | Compound A2 Concentration in Plasma (ng/ml) | | | | |
|---|---|---|---|---|---|
| | Time point (h) | Mouse 1 | Mouse 2 | Mouse 3 | Mean | SD |
| PO (30 mg/kg) | 2 | 59.0 | *6042.8 | 230.4 | 144.7 | 121.2 |
| | 4 | 38.9 | 102.8 | 81.2 | 74.3 | 32.5 |
| | 7 | 105.7 | 76.8 | *301.8 | 91.3 | 20.4 |

| | Compound A1 Concentration in Plasma (ng/ml) | | | | |
|---|---|---|---|---|---|
| | Time point (h) | Mouse 1 | Mouse 2 | Mouse 3 | Mean | SD |
| IV (30 mg/kg) | 2 | 69.6 | 124.0 | 38.8 | 77.4 | 43.2 |
| | 4 | 46.4 | 20.2 | 20.9 | 29.2 | 14.9 |
| | 7 | 36.5 | 5.9 | 8.3 | 16.9 | 17.0 |

TABLE 1-continued

Compound A1, A2, and A4 Concentration in Mouse Plasma following PO and IV administration at 2, 4, and 7 hours.

| | Compound A1 Concentration in Plasma (ng/ml) | | | | |
|---|---|---|---|---|---|
| | Time point (h) | Mouse 1 | Mouse 2 | Mouse 3 | Mean | SD |
| PO (30 mg/kg) | 2 | 21.0 | *899.2 | 59.7 | 40.4 | 27.3 |
| | 4 | 48.9 | 89.8 | 20.0 | 52.9 | 35.1 |
| | 7 | 12.1 | 24.1 | 9.3 | 15.2 | 7.8 |

*outliers

| | Compound A4 Concentration in Plasma (ng/ml) | | | | |
|---|---|---|---|---|---|
| | Time point (h) | Mouse 1 | Mouse 2 | Mouse 3 | Mean | SD |
| IV (30 mg/kg) | 2 | 94.2 | 172.3 | 71.0 | 112.5 | 53.1 |
| | 4 | 20.8 | 28.8 | 20.6 | 23A | 47 |
| | 7 | 24.1 | 5.6 | 0.8 | 10.2 | 12.3 |

| | Compound A4 Concentration in Plasma (ng/ml) | | | | |
|---|---|---|---|---|---|
| | Time point (h) | Mouse 1 | Mouse 2 | Mouse 3 | Mean | SD |
| PO (30 mg/kg) | 2 | *20.2 | 641.8 | 409.6 | 5257 | 164.2 |
| | 4 | 33.4 | *127.5 | 33.8 | 33.6 | 0.3 |
| | 7 | 33.2 | 22.9 | 30.9 | 29.0 | 5.4 |

*outliers

Preparation of Washed Human Platelets

Citrated whole blood was centrifuged (200 g for 10 min) to isolate platelet-rich plasma. Platelet-rich plasma was treated with acid citrate dextrose (2.5% sodium citrate, 1.5% citric acid, 2.0% D-glucose) and apyrase (0.02 U/mL), and then centrifuged (2000 g for 10 mins) to pellet the platelets. Platelets were resuspended at $3.0 \times 10^8$ platelets/mL in Tyrode's buffer (10 mM HEPES, 12 mM $NaHCO_3$, 127 mM NaCl, 5 mM KCl, 0.5 mM $NaH_2PO_4$, 1 mM $MgCl_2$, and 5 mM glucose) unless otherwise stated.

Platelet Appreciation

Figure 2:
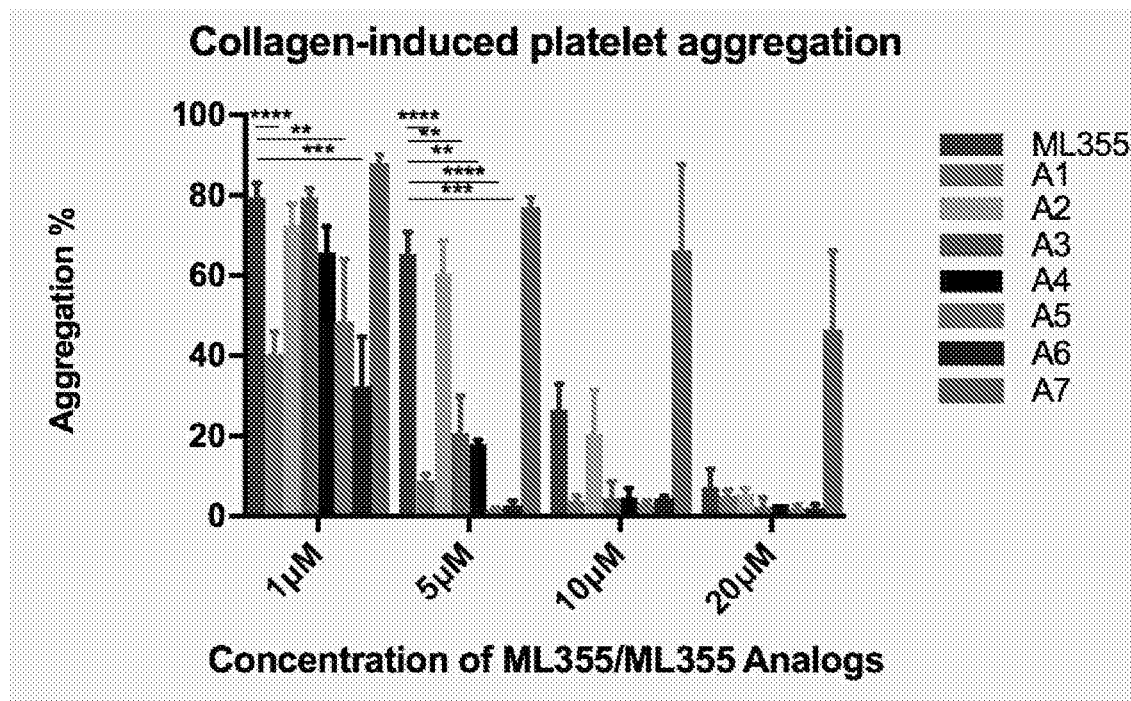
FIG. 2 depicts the percentage of collagen-induced platelet aggregation for compounds A1-A7 at 1 µM, 5 µM, 10 µM, and 20 µM, as further described in the Examples section.
Figure 3:
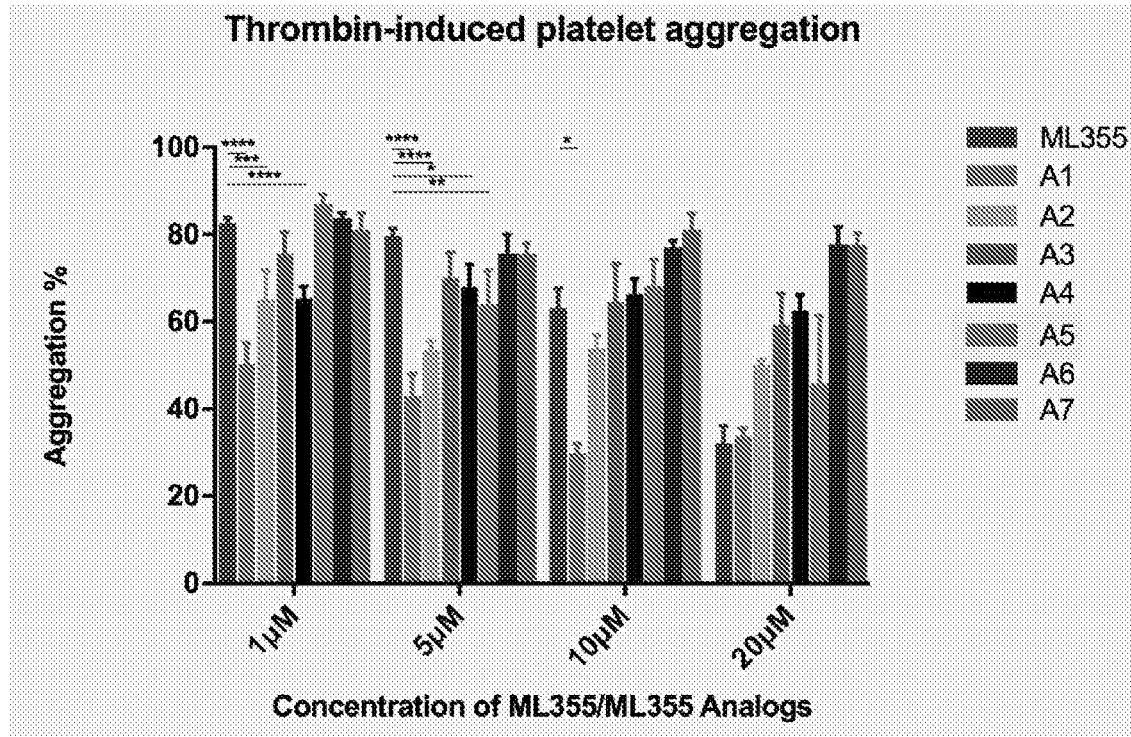
FIG. 3 depicts the percentage of thrombin-induced platelet aggregation for compounds A1-A7 at 1 µM, 5 µM, 10 µM, and 20 µM, as further described in the Examples section.

Washed human platelets were prepared at $3 \times 10^8$ platelets/ml and aggregation was measured in a 4-channel Lumi-aggregometer (Chonolog Inc, Model 700D) under stirring conditions at 1100 RPM at 37° C. Platelets were incubated with increasing concentrations of the compounds described herein (1 μM to 20 μM) for 10 minutes and platelet aggregation was induced by an $EC_{80}$ concentration of thrombin or collagen. Each condition was repeated with platelets from 5 independent volunteers (N=5). Inhibition of aggregation was considered statistically significant if there was a significant decrease in aggregation compared to ML355 treated conditions. *, $P<0.05$; , $P<0.01$; *, $P<0.001$; ****, $P<0.0001$. See FIG. 2 and FIG. 3.

In Vivo Pharmacokinetics Following Oral Administration in Mice

Compound A1 was orally administered to mice (30 mg/kg), and the drug concentration of plasma in mice (n=3) was monitored at 8 time points (0.25, 0.5, 1, 2, 4, 8, 12, and 24 hours) and assessed by PK analysis as described, supra.

Compound Pre-Treatments on Experimental Mice for In Vivo Studies

C57BL/6 wild-type (WT) control mice were purchased from Jackson Laboratories (Bar Harbor, Me., USA) and housed in the research facility at the University of Michigan. Compound A1 was synthesized and specifically formulated in Polyethylene Glycol 300 (PEG 300) for oral gavage dosing in mice for in vivo thrombosis and hemostasis studies. For laser-induced cremaster arteriole thrombosis model, mice were treated with compound A1 (3 mg/kg) or with PEG 300 via oral administration 2 times per day for 2 days prior to intravital microscopy studies on the third day.

Laser-Induced Cremaster Arteriole Thrombosis Model

Adult mice (10-12 weeks old) were anesthetized as described above and surgically prepared as described in detail, and a tracheal tube was inserted to facilitate breathing. The cremaster muscle was prepared and perfused with preheated bicarbonate-buffered saline throughout the experiment. DyLight 488-conjugated rat anti-mouse platelet GP1b8 antibody (0.1 μg/g; EMFRET Analytics) and Alexa Fluor 647-conjugated anti-fibrin (0.3 μg/g) or Alexa Flour 647 rat-anti mouse CD62P (3 μg/mouse) were administered by a jugular vein cannula prior to vascular injury. Multiple independent thrombi were induced in the arterioles (30-50 μm diameter) in each mouse by a laser ablation system (Ablate! photoablation system; Intelligent Imaging Innovations, Denver, Colo., USA). Images of thrombus formation at the site of injured arterioles were acquired in real-time under 63× water-immersion objective with a Zeiss Axio Examiner Z1 fluorescent microscope equipped with solid laser launch system (LaserStack; Intelligent Imaging Innovations) and high-speed sCMOS camera. All captured images were analyzed for the change of fluorescent intensity over the course of thrombus formation after subtracting fluorescent background defined on an uninjured section of the vessel using the Slidebook program.

Figure 4:
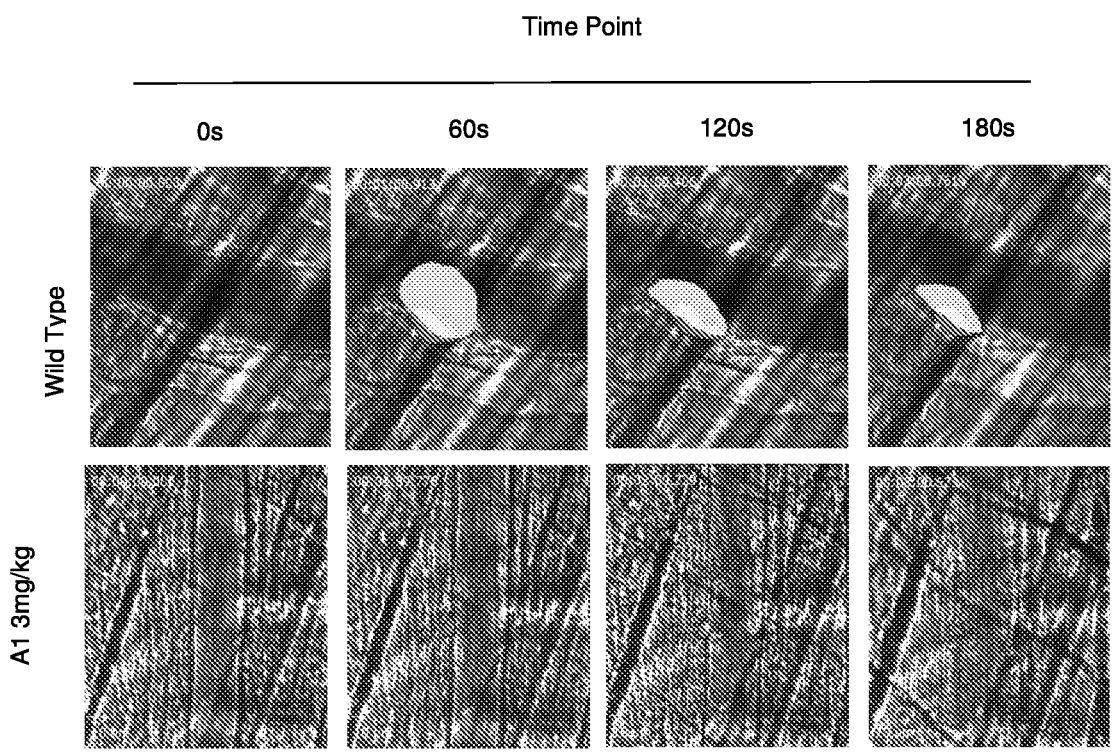
FIG. 4 depicts representative images of platelet accumulation (green) and fibrin formation (red) in growing thrombi in cremaster arterioles in a wild-type ("WT") control animal treated with polyethylene glycol ("PEG"; control, upper) and WT treated with compound A1 (3 mg/kg, twice a day for 2 days; lower), as further described in the Examples section, demonstating that platelet 12(S)-lipoxygenase ("12-LOX") inhibition impairs thrombus formation in laser-induced cremaster arteriole thrombosis models.

Representative images of platelet accumulation (green) and fibrin formation (red) in growing thrombi in cremaster arterioles in a wild-type (WT) control animal treated with polyethylene glycol (PEG; control, upper) and WT treated with compound A1 (3 mg/kg, twice a day for 2 days; lower) are shown in FIG. 4

Anti-GPIX-Induced HITT Model for Luna Thrombosis

Adult transgenic mice (10-12 weeks old) expressing the human FcγRIIa receptor on their platelets were anesthetized as described above and were orally gavaged with 15 mg/kg of A1 or control vehicle 30-minutes prior to IV bolus injection of 0.75 mg/kg anti-GPIX to induce activation of the FcγRIIa receptor on the platelets to mimic heparin-induced thrombocytopenia and thrombosis ("HITT") in the mouse. The anti-GPIX antibody was conjugated to DyLight 488 to visualize its binding to platelets and platelet accumulation in the lung. 4 hours post-anti-GPIX induction, the animals were sacrificed and the lungs were visualized using the Li—COR Odyssey imager.

Figure 5:
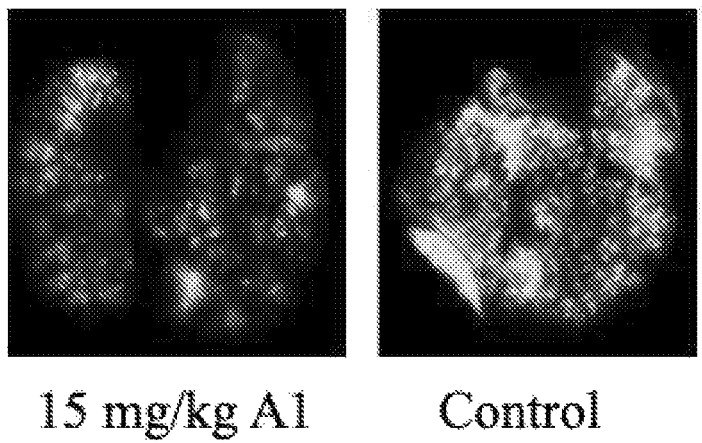
FIG. 5 depicts representative images of platelet accumulation (green) in the mouse lungs from control (PEG vehicle) and A1-treated (15 mg/kg) mice four hours following heparin-induced thrombocytopenia and thrombosis ("HITT"), as further described in the Examples section, demonstrating that the compounds disclosed herein can inhibit thrombocytopenia and thrombosis in mouse lungs.

Representative images of platelet accumulation (green) in the mouse lungs from control (PEG vehicle) and A1-treated (15 mg/kg) mice are shown in FIG. 5

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound of Formula (I), or a pharmaceutically acceptable salt thereof:

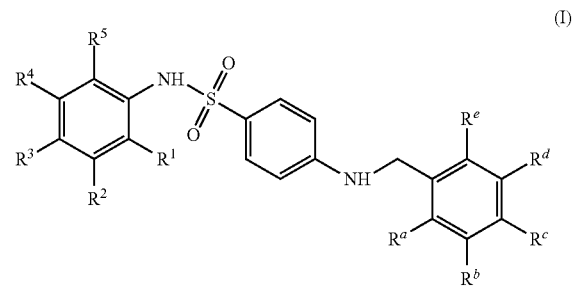

(I)

wherein:

$R^2$ is halo, $C_{1-3}$fluoroalkyl, $C_{3-8}$fluorocyloalkyl, $OC_{1-3}$fluoroalkyl, or $OC_{3-8}$fluorocyloalkyl;

each of $R^1$, $R^3$, $R^4$, and $R^5$ independently is H, halo, $C_{1-3}$fluoroalkyl, $C_{3-8}$fluorocyloalkyl, $OC_{1-3}$fluoroalkyl, or $OC_{3-8}$fluorocyloalkyl;

each of $R^a$ and $R^b$ independently is OH, $OC_{1-3}$alkyl, $C_{1-3}$fluoroalkyl, $C_{3-8}$fluorocyloalkyl, $OC_{1-3}$fluoroalkyl, $OC_{3-8}$fluorocyloalkyl, or halo; and each of $R^c$, $R^d$, and $R^e$ independently is H, OH, $OC_{1-3}$alkyl, $C_{1-3}$fluoroalkyl, $C_{3-8}$fluorocycloalkyl, $OC_{1-3}$fluoroalkyl, $OC_{3-8}$fluorocyloalkyl, or halo.

2. The compound of claim 1, wherein $R^2$ is halo.

3. The compound of claim 1, wherein $R^2$ is $C_{1-3}$fluoroalkyl, $C_{3-8}$fluorocyclolalkyl, $OC_{1-3}$fluoroalkyl, or $OC_{3-8}$fluorocyloalkyl.

4. The compound of claim 1, wherein each of $R^1$, $R^3$, $R^4$, and $R^5$ is H.

5. The compound of claim 1, wherein one or more of $R^1$, $R^3$, $R^4$, and $R^5$ is halo, $C_{1-3}$fluoroalkyl, $C_{3-8}$fluorocyloalkyl, $OC_{1-3}$fluoroalkyl, or $OC_{3-8}$fluorocyloalkyl.

6. The compound of claim 1, wherein $R^1$ is H or F; $R^2$ is Cl, $CF_3$, or

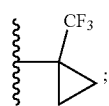

$R^3$ is H or F; $R^4$ is H; and $R^5$ is H.

7. The compound of claim 1, wherein each of $R^a$ and $R^b$ independently is OH or $OC_{1-3}$alkyl.

8. The compound of claim 1, wherein one of $R^a$ and $R^b$ is OH or $OC_{1-3}$alkyl; and the other of $R^a$ and $R^b$ is $C_{1-3}$fluoroalkyl, $C_{3-8}$fluorocyloalkyl, $OC_{1-3}$fluoroalkyl, $OC_{3-8}$fluorocyloalkyl, or halo.

9. The compound of claim 1, wherein each of $R^a$ and $R^b$ independently is $C_{1-3}$fluoroalkyl, $C_{3-8}$fluorocyloalkyl, $OC_{1-3}$fluoroalkyl, $OC_{3-8}$fluorocyloalkyl, or halo.

10. The compound of claim 1, wherein $R^c$, $R^d$, and $R^e$ are each H.

11. The compound of claim 1, wherein one or more of $R^c$, $R^d$, and $R^e$ is halo, $C_{1-3}$fluoroalkyl, $C_{3-8}$fluorocyloalkyl, $OC_{1-3}$fluoroalkyl, or $OC_{3-8}$fluorocyloalkyl.

12. A compound selected from the group consisting of:

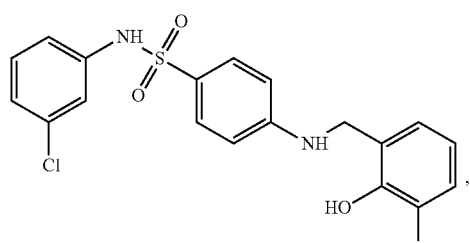

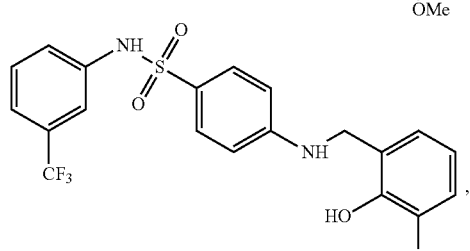

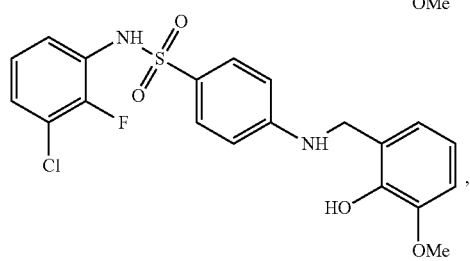

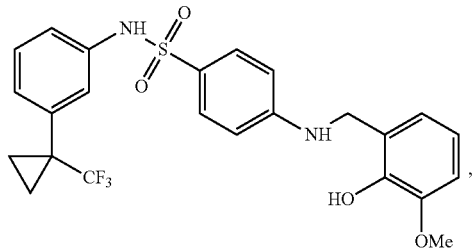

-continued

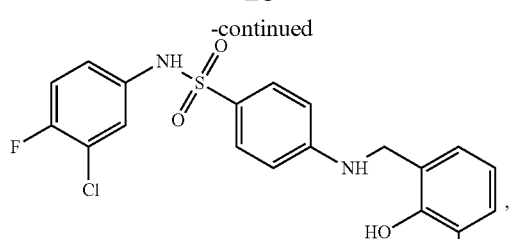

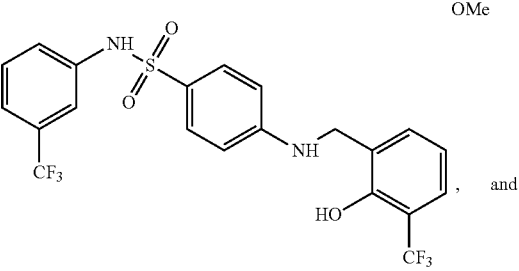

, and

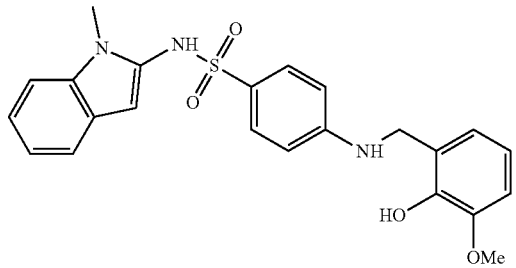

or a pharmaceutically acceptable salt thereof.

13. A pharmaceutical composition comprising the compound of claim 1 and a pharmaceutically acceptable carrier.

14. A method of inhibiting (S)-Lipoxygenase ("12-LOX") activation in a cell comprising contacting the cell with the compound of claim 1 in an amount effective to inhibit 12-LOX activation.

15. A method of inhibiting platelet factor 4 ("PF4") release in cell comprising contacting the cell with the compound of claim 1 in an amount effective to inhibit PF4 release.

16. A method of inhibiting PF4-heparin complex formation in cell comprising contacting the cell with the compound of claim 1 in an amount effective to inhibit PF4-heparin complex formation.

17. A method of inhibiting platelet activation in a cell comprising contacting the cell with the compound of claim 1 in an amount effective to inhibit platelet activation.

18. A method of inhibiting thrombin, protease-activated receptor-4 ("PAR4"), and/or glycoprotein VI ("GPVI") signaling in a cell comprising contacting the cell with the compound of claim 1 in an amount effective to inhibit PAR4 and/or GPVI signaling.

19. A method of treating or preventing a thrombotic disorder in a subject in need thereof comprising administering to the subject a therapeutically effective amount of the compound of claim 1.

20. A method of treating thrombocytopenia in a subject in need thereof comprising administering to the subject a therapeutically effective amount of the compound of claim 1.

* * * * *